United States Patent
Burnham

[11] Patent Number: 5,496,292
[45] Date of Patent: Mar. 5, 1996

[54] CATHETER WITH IRREGULAR INNER AND/OR OUTER SURFACES TO REDUCE TRAVELLING FRICTION

[76] Inventor: Warren Burnham, Drawer 317, Glens Falls, N.Y. 12801

[21] Appl. No.: 140,124

[22] PCT Filed: May 4, 1992

[86] PCT No.: PCT/US92/03668

§ 371 Date: Nov. 2, 1993

§ 102(e) Date: Nov. 2, 1993

Related U.S. Application Data

[63] Continuation-in-part of Ser. No. 695,522, May 3, 1991, Pat. No. 5,244,619.

[51] Int. Cl.$^6$ ............................................. A61M 25/00
[52] U.S. Cl. ........................ 604/282; 604/280; 128/657
[58] Field of Search .................................. 604/280, 282, 604/264, 270; 128/657, 772

[56] References Cited

U.S. PATENT DOCUMENTS

| | | |
|---|---|---|
| 3,419,010 | 12/1968 | Williamson. |
| 3,428,046 | 2/1969 | Remer. |
| 3,618,613 | 11/1971 | Schulte. |
| 3,783,454 | 1/1974 | Sausse. |
| 4,137,452 | 3/1982 | Russo et al. ............................ 604/282 |
| 4,705,511 | 11/1987 | Kocak. |
| 4,764,324 | 8/1988 | Burnham. |
| 4,832,681 | 5/1989 | Lenck. |
| 4,917,666 | 4/1990 | Solar. |
| 4,927,413 | 5/1990 | Hess. |
| 4,950,232 | 8/1990 | Ruzicka. |
| 4,955,859 | 9/1990 | Zilber. |
| 4,955,862 | 9/1990 | Sepetka. |
| 4,998,919 | 3/1991 | Schnepp-Pesch et al. ......... 604/280 X |
| 5,125,909 | 6/1992 | Heimberger. |
| 5,151,105 | 9/1992 | Kwan-Gett .......................... 604/280 X |
| 5,337,733 | 8/1994 | Bauerfeind et al. ................. 604/282 X |

FOREIGN PATENT DOCUMENTS

| | | |
|---|---|---|
| 1618422 | 1/1991 | U.S.S.R.. |
| 2207902 | 2/1989 | United Kingdom. |

*Primary Examiner*—Sam Rimell
*Attorney, Agent, or Firm*—Ronald P. Kananen

[57] ABSTRACT

A catheter having an irregular outer diameter and/or an irregular inner diameter caused by embedment of a reinforcing member, thereby reducing sliding friction compared to conventional smooth-wall catheters.

8 Claims, 6 Drawing Sheets

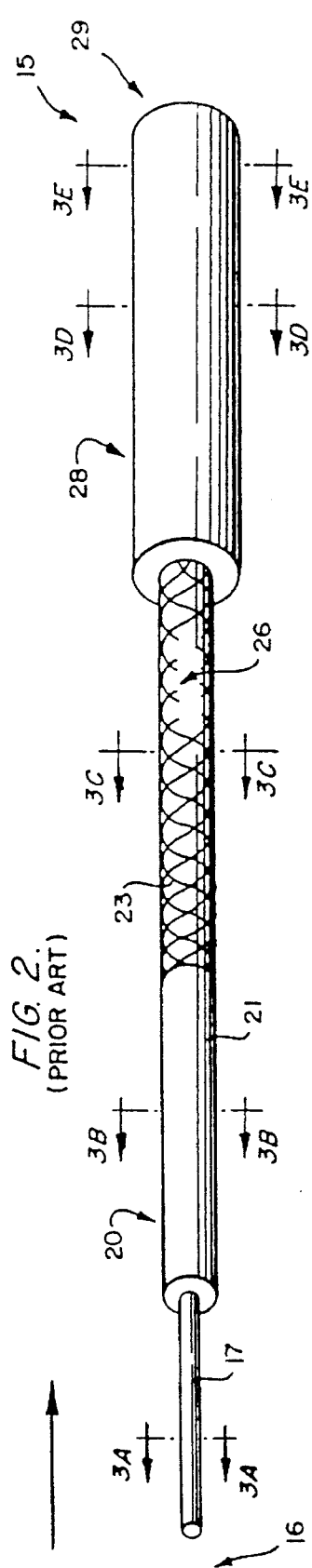
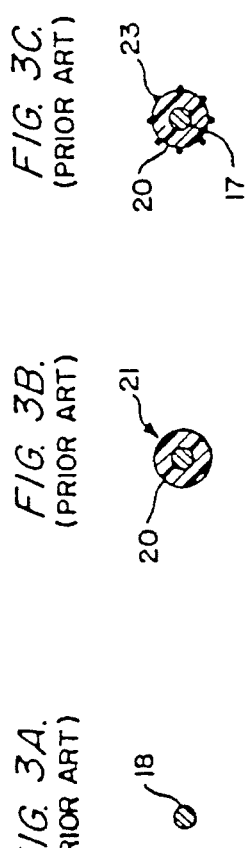
FIG. 2. (PRIOR ART)
FIG. 3A. (PRIOR ART)
FIG. 3B. (PRIOR ART)
FIG. 3C. (PRIOR ART)
FIG. 3D. (PRIOR ART)
FIG. 3E. (PRIOR ART)

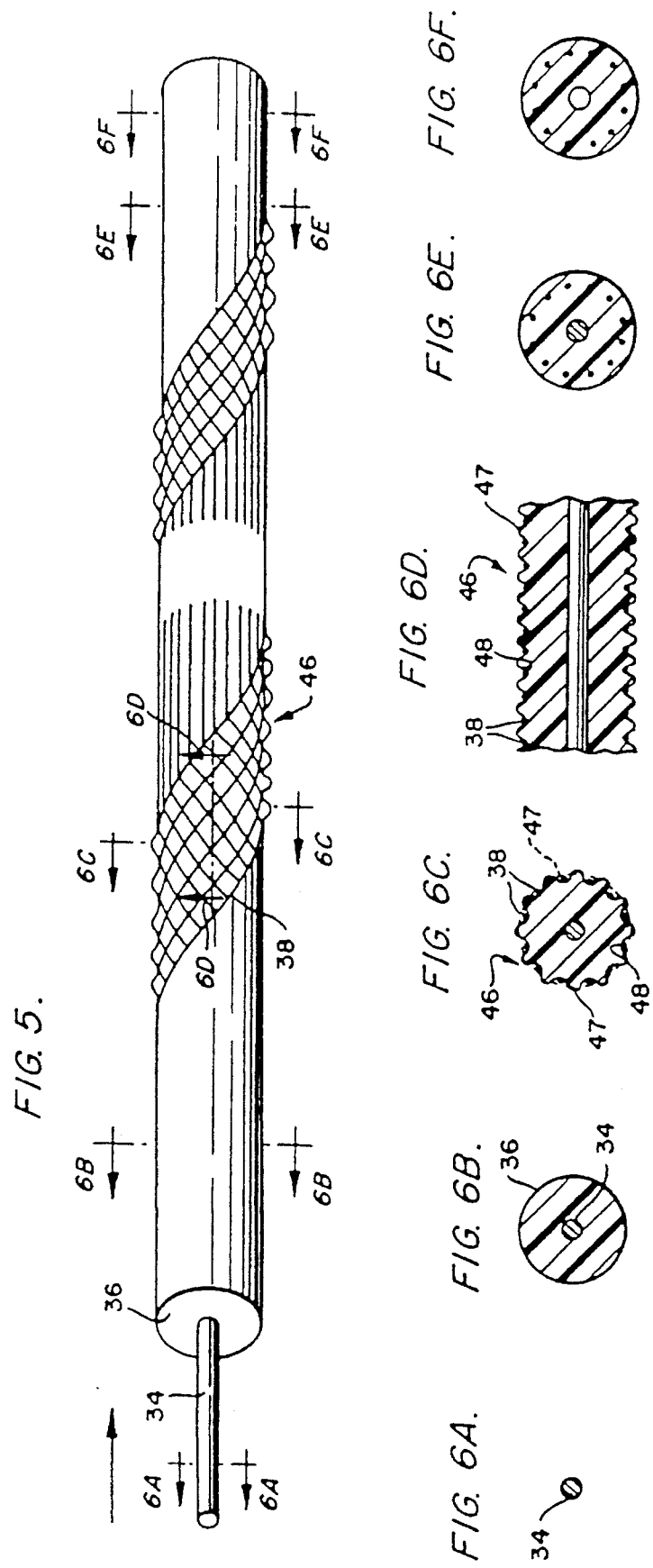

CATHETER WITH IRREGULAR INNER AND/OR OUTER SURFACES TO REDUCE TRAVELLING FRICTION

This application is a continuation-in-part of U.S. patent application Ser. No. 07/695,522 filed May 3, 1991, which issued as U.S. Pat. No. 5,244,619 on Sep. 14, 1993.

BACKGROUND OF THE INVENTION

This invention relates to a method of making tubular products, especially catheters. More particularly, this invention relates to a method for making a reinforced catheter having an irregular lumen surface to reduce friction when used as a guiding catheter for the passage of another catheter through the lumen or the rotation of another catheter within the lumen. Still more particularly, this invention relates to a method of making a catheter wherein either or both elongated axial surfaces of a catheter are modified to decrease mechanical friction due to fluid coupling by causing the surfaces to have a non-linear or non-smooth character, thus to limit contact area with any adjacent structure to relatively small areas or line or points rather than the entire geometric surface or relatively large surfaces.

As explained in U.S. Pat. No. 4,764,324, the art of manufacturing tubes, pipes or cannulae by extruding a plastic material to produce significant quantities of tubing is fairly well developed. In many instances, it is desirable to use reinforcement in the tubes or pipes to increase the pressure, tensioning, or torque-carrying capacities of those tubes or pipes. Ordinary plastic garden hose reinforced with filament is a common example of such a product made according to prior art techniques, as is a catheter for applications in the medical field.

Catheters of the type contemplated are relatively thin and flexible tubes which include inner and outer plastic layers with a wire sheathing embedded between the layers wherein the wire sheathing is either braided or cross-wound to obtain maximum torsional rigidity and a satisfactory longitudinal flexibility. A convention prior art process for making a reinforced extruded catheter is a three-step process. In the first step, a mandrel having an outside diameter about equal to the desired inside diameter of the finished catheter is passed through suitable extrusion tooling to cause a tubular jacket or sheath of the catheter material to form around the mandrel. In this step, the outside diameter of the first extrusion layer on the mandrel is smaller than the desired finished outside diameter of the finished catheter. Next, the inner core tube formed in the first step as described above is processed by suitable machinery to cause a pattern of reinforcing materials, such as wires, fibers, or monofilaments, for example, to be laid along and/or around or partially into and in contact with the surface of the core tube. Next, the composite intermediate structure of the inner core tube and the reinforcing layer thus applied is again passed through suitable extrusion tooling equipment to deposit a second layer of catheter material around and bonded to the composite thereby encapsulating the now reinforced inner core tube forming essentially a single structure. The outside diameter of the second layer of extrusion is approximately equal to the desired finished outside diameter of the catheter. Subsequently, finishing and polishing operations can be performed and a composite thus constructed cut to its desired length. The mandrel, if any, is then extracted by lengthwise pulling, leaving the hollow catheter tubing with reinforced walls. That process produces a catheter with smooth, uninterrupted inner and outer circumferential surfaces.

U.S. Pat. No. 4,764,324 to the applicant herein constitutes a significant improvement on that three-step process by recognizing that heating the polymer substrate, or the reinforcing material and a polymer substrate beneath it, during a process of manufacturing a catheter, while simultaneously applying axial tension to the reinforcement, will cause the reinforcement material to deform or penetrate the original surface of the catheter body polymer and thus penetrate into such a surface. The distance to which the reinforcement material sinks into the underlying polymer is highly controllable and repeatable depending on the conditions of the relative temperatures of the catheter body and the reinforcement material, as well as on the tension exerted on the reinforcing material, and the physical characteristics of the polymer from which the catheter is made. Thus, by controlling these parameters, the radial position of the reinforcement in the wall of the catheter can be simply but accurately followed. In the '324 patent, it had been noted that the polymer thus softened and deformed or penetrated but remaining outside of the new smaller diameter of the reinforcement structure produces a somewhat peaked or waffled contour in those locations where the polymer has exuded between the strands or filaments of the reinforcement and extends radially outwardly beyond the reinforcement to an extent where it can be worked to form the outer wall of the catheter body. However, the art suggested that smooth-walled catheters were desirable and users demanded such devices.

Accordingly, catheters made by either of the two processes noted above produced a catheter witch a smooth inner diameter or bore well, or lumen, as well as a smooth, outer diameter wall to form a smooth surface composite construction of polymer containing the imbedded reinforcement between the now smooth inner and outer surfaces.

In fact, for most reinforced medical tubing structures, placement of the reinforcement strand is desired at or near the mid-wall point of the structure. In the '324 patent, the depth of radial placement of the reinforcement strand is chiefly controlled by the degree of heat softening of the substrate at the time the reinforcement impinges the surface under essentially constant application tension.

Among medical tube structures are those that are used as mechanical guides or sheaths. One such tube is the guide for balloon catheters in the practice of angioplasty. In this use, since a balloon-carrying catheter is to slide through the previously-placed guiding catheter, it is desired to reduce internal friction between the guide tube and the balloon catheter to a minimum.

A smooth-walled guiding catheter, even one with a lining of a low friction material, such as a Teflon\brand material, can exhibit a considerable drag friction due to fluid coupling where a think film of fluid "locks" the surface of the balloon to the catheter wall. An example of this phenomenon when air is the fluid can be found when meshing precision gauge blocks in a machine shop which, if pushed together tightly, will stick together even though there are no forces such as magnetism present. This occurs because the joint line between the blocks is so small that it does not readily allow air to enter the blocks to cause them to separate. Similarly, in the case of smooth-walled catheters and balloons, rubbing against the smooth guide tube wall displaces all but essentially a monolayer of the fluid present over a relatively large contact area, A=d1 where d is the diameter of the lumen or I.D. of the tube; and 1 is the length of contact, allowing forces of molecular friction to create an unacceptably high drag friction.

Accordingly, it is a problem in the art, even in the use of standard smooth-bore catheters, and even when stiffness and torque properties are excellent and friction is low when dry, that high levels of fluid friction are experienced as soon as blood or injectate are present to make the fluid friction with the tube unacceptable.

Accordingly, it is an overall problem addressed by this invention to develop a catheter and guide-tube pair which exhibit a marked reduction in axial and rotational drag forces during manipulation due to virtually complete elimination of viscous coupling between the adjacent surfaces.

Accordingly, it is an object of this invention to provide a catheter having an inner bore or lumen with an irregular surface to reduce contact friction when in use.

It is another overall object of this invention to provide a method and apparatus wherein either or both surfaces of a tubular object or the outer surface of a solid object are modified in such a way as to decrease mechanical friction due to fluid coupling by causing the surfaces to have a non-lineal or non-smooth character, thus limiting contact area within the adjacent structure to small areas of points or lines rather than the entire geometric surface.

It is another overall object of this invention to provide a method and apparatus for producing a catheter with modified and controlled surface geometry by processes of embossing patterns on the outside surface and molding patterns into tubular inner surfaces.

It is still another object of this invention to provide a tubular catheter having a modified lumen surface wherein a reinforcing braid is submerged in a layer at the time of pattern of generation by use of a correctly sized die heated to a point where it heats and pushes the reinforcement (or pattern) into a substrate to cause waffle-like distortion of an outer wall surface of the structure.

These and other objectives of the invention will become apparent from the drawings and the detailed description of the invention which follows.

SUMMARY OF THE INVENTION

Directed to achieving the forgoing objects and overcoming the problems of the prior art, this invention relates to a tubular object, such as a reinforced catheter, wherein the surface of the interior bore or lumen is irregular. In particular, the irregularity in the interior bore or lumen surface of the catheter is caused by placement of a reinforcement strand applied according to the teachings of the Applicant's prior U.S. Pat. No. 4,764,324 to a location proximate but not through the interior wall, causing irregularity in the lumen wall. Accordingly, the inner surface geometry is modified by displacement of the tube wall into the mandrel, thus exhibiting on the I.D. wall radially-raised ridges of maximum height directly under a reinforcement strand. Since the reinforcement strands are almost always in the form of a helical wrap along the axis of the tube, during the manufacturing process, the raised ridges take the form of helices along the tubing with the same hand as the innermost strands as applied.

The interior lumen or bore of the tubular catheter thus has its normally smooth surface interrupted by a pattern which eliminates the problem of fluid coupling because contact between stationary and moving members is along the line or innermost surface of the raised ridges, rather than across and along the entire lumen surface.

In another aspect, the applicant's invention relates to surface modification of the external surface of a solid or tubular object, such as the catheter, to reduce friction as noted above, especially when the catheter is moved through or rotated within a guiding catheter. The exterior surface of the object to which a reinforcement was applied, according to the teachings of the '324 patent, exhibit an elongated diamond-like or waffle-like pattern generated on the outer surface by the entry by right and left hand reinforcement helices. Rather than completely smooth over the "diamonds" or "waffles" a smoothing step is eliminated, or an oversized die is used to perform an intentionally incomplete smoothing step, leaving a pattern of smooth-tipped waffles or diamonds on the outside tube surface. While normally such a rough outer tube surface would be discarded as unsuitable for vascular contact, it was found that such a surface has significant advantages when the tube was used to slide concentrically down the lumen of an outer tube acting as a guide tube or to be rotated within a guide tube.

According to another aspect of the invention, a method of making such a tube is provided according to the steps of the '324 patent comprising a continuous method for making a finished reinforced catheter made from a polymeric material exhibiting a range of apparent viscosity proportional to temperature and having an inner diameter and an outer diameter with reinforcement completely embedded within the wall of the tube between the inner diameter and the outer diameter.

The method comprises the steps of providing as an interim structure an extruded, mandrelized polymeric catheter body having an outer diameter about equal to the outer diameter of the finished catheter; providing the mandrelized catheter body in a condition heated to a state sufficient to prevent a reinforcing member under tension to be submerged completely beneath an outer surface of the heated tubular structure to a location adjacent to the inner diameter; and[ applying the reinforcing member at the outer surface of the heated interim mandrelized catheter body under sufficient tension to cause the reinforcing member to travel inwardly through the polymeric outer surface to a predetermined extent to deform the outer surface relative to the reinforcing member by a volume about equal to the volume of the reinforcing material added[ to the tubular structure. In one aspect of the invention, the process contemplates not smoothing the irregular surface so formed or smoothing the outer surface of the reinforcing catheter with an oversized die to permit the outer surface to remain irregular.

In another aspect of the invention, the reinforcing material added to the tubular structure is located accurately in the wall of the body adjacent to or near or sufficiently near the inner diameter to cause a distortion thereof, thus to cause inner surface irregularity or irregular contours determined by the reinforcement. Thus, the combination of temperature and material of the catheter and tension on the reinforcing member controlling the location of the reinforcing member to the position noted will produce a catheter having the thus-modified surface structure(s).

These and other features of the invention will become apparent from the detailed description of the invention which follows, taken with the accompanying drawings.

BRIEF DESCRIPTION OF THE DRAWINGS

In the drawings:

FIG. 2 is a pictorial diagram partially in perspective, showing the catheter structure as it progresses through the manufacturing process diagrammed in FIG. 1;

FIG. 3, including FIGS. 3A–3E, are cross section of the composite catheter structure at various steps in the prior art process depicted in FIGS. 1 and 2;

FIG. 5 is a pictorial diagram, partially in perspective, showing the structure of the invention at various stages in the manufacturing process of FIG. 4;

FIG. 6, including FIGS. 6A–6F, illustrates cross sections of the composite structure at various stages in the process shown in FIGS. 4 and 5 according to the invention;

FIG. 7 is a series of cross-sectional views of distortions of the interior wall and mandrel according to the invention, wherein

DETAILED DESCRIPTION OF THE PREFERRED EMBODIMENTS

Figure 1:
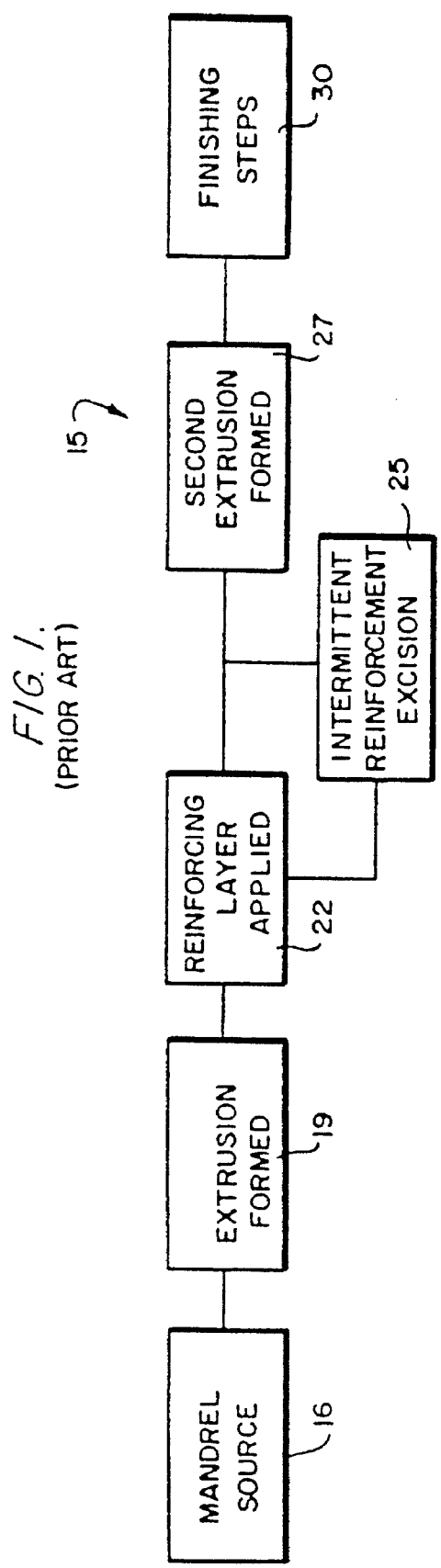
FIG. 1 is a block diagram of a prior art process for manufacturing an intermittently reinforced catheter with an unitary reinforced tip.

FIGS. 1–3 describe in greater detail a prior art process for manufacturing a reinforced tube, for example, a catheter, as designated generally by the reference numeral 15. As shown in FIGS. 1–3 a mandrel 17, from a mandrel source 16, comprises an elongated tubular or solid form 17 having a generally circular cross section (FIG. 3A) is passed through an extruder 19 to provide a sheath 20 of plastic material about the mandrel 17. The mandrel 17 has an outside diameter equal to the desired inside diameter of the finished catheter 15. The innermost layer of the catheter wall is formed from the sheath 20 to form a base tube for the finished catheter and has an inside diameter equal to the outside diameter of the mandrel 17. The plastic sheath 20 about the mandrel 17 during the first extrusion step has an outside diameter which is smaller than the desired finished outside diameter of the finished catheter.

The inner base tube 21 formed as described above is processed by suitable machinery 22, known to the art, to cause a pattern of reinforcing material 23 to be laid along and/or around or partially into or in contact with the outer surface of the core tube 21. By way of example, the reinforcing material may include wires, fibers or monofilaments. Where desired, the composite catheter structure with the reinforcing material 23 may be processed to intermittently excise a portion of the reinforcement, as shown generally by step 25. In performing this step, the reinforcement material thus formed is physically removed along spaced portions of the core tube 21, as shown at portion 26 of FIG. 2. Thereafter, the core tube 21 with reinforcement spacedly excised is passed again through an extruder 27 to form a second layer 28 of extruded wall material as a sheath and bonded to the composite to produce a composite structure having an outer diameter of the catheter. In performing this step, therefore, the reinforcing layer 23 (whether or not partially excised) is thus embedded in the wall of the final composite catheter structure 28, which wall comprises two radially located sequentially applied extrusion layers bonded together to form a structurally single tube wall. Finally, in the step designated generally by the reference numeral 30, the composite thus constructed may have its wall smoothed to a tolerance of about ±0.0005 inches; is cut to its desired length; and the mandrel 17, is extracted by lengthwise pulling leaving the hollow catheter tubing with intermittent or continuous reinforced walls.

Figure 4:
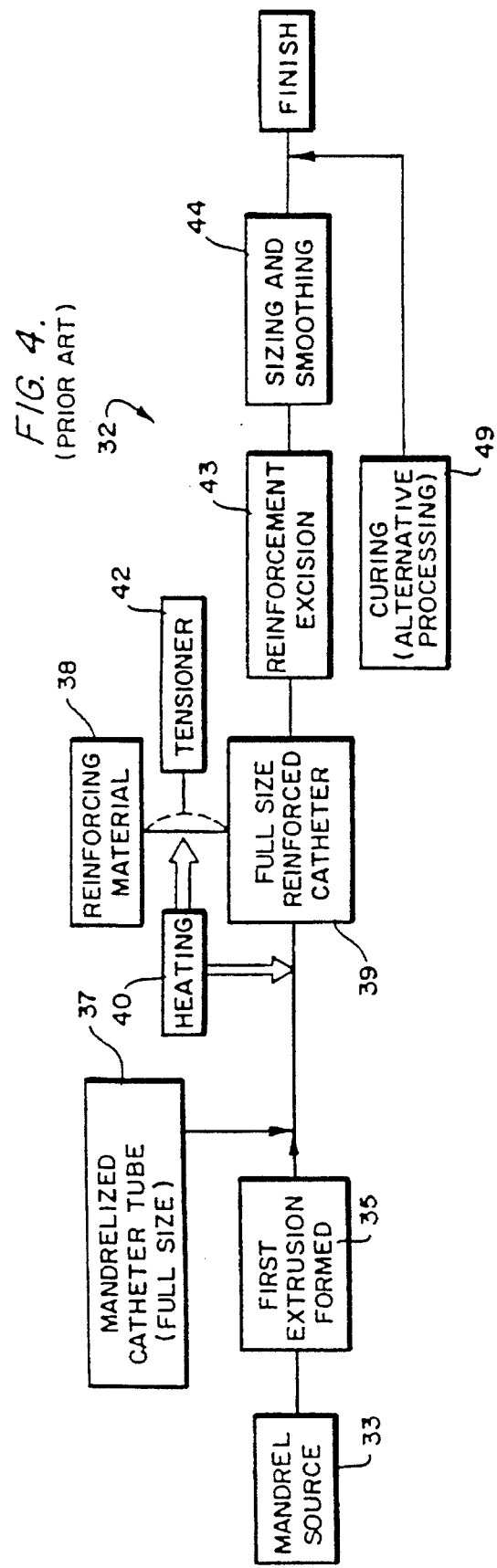
FIG. 4 is a block diagram of an improved prior art the process suitable for making the catheter according to the invention.

A process for making the tube, such as a reinforced catheter, according to the invention is best seen in its preferred embodiment in FIGS. 4–6. In FIG. 4, the prior art Burnham process is designated generally by the reference numeral 32. As a starting material for the process 32, a mandrel 34 from a mandrel source 33 is passed through an extruder 35 to deposit a sheath 36 about the mandrel 34 in a manner somewhat similar to the first extrusion step of FIGS. 1 to 3. However, the outside diameter of the extrusion here is approximately equal to the full outside diameter of the finished catheter and is the only extrusion step performed.

Reinforced material 38 is applied to the mandrel/tubing composite structure 39 in a manner similar to that described in connection with FIG. 1. However, it has been found that the application of heat by a suitable heat source 40 to the mandrelized wall tubing acting as a starting material and/or to the reinforcing material 38, while simultaneously tensioning the reinforcing material by a tensioning device 42 will cause the reinforcing material when applied to the original surface of the catheter body to sink into such surface and to penetrate or deform it. The heat thus applied to a thermoplastic material forming the catheter body causes the thermoplastic polymer to soften to an extent sufficient to permit such penetration or deformation.

It has been found that the distance into which the reinforcement material penetrates beneath the surface of the catheter body and thus sinks into the underlying polymer is highly controllable and repeatable. That distance is a function of the relative temperatures of the catheter body and/or the reinforcement material, as well as the simultaneous tension exerted on the reinforcing material by the tensioning device, and the material of the body. Thus, by way of example, if the temperatures applied to the catheter body and the reinforcing material are controlled within toleranced limits, for a given catheter body made from a known polymer exhibiting known viscosity as a function of temperature, the depth of penetration of the reinforcing material can be determined for a given process rate and time of application virtually solely by the degree of tensioning applied by the tensioning device.

An alternative practice of the process, assuming that the tensioning is fixed within toleranced limits, the degree of heating of the catheter body and/or the reinforcement material, will similarly control the dept of penetration at a constant process speed. In its simplest form, controlling the temperature of the heat source 40 will control the degree of heating of the catheter body composite at that stage in the process. Since the process is practiced on a continuous basis, the heating temperature may also be controlled by the speed of the process, by way of example, by passing the mandrelized catheter body through a heat source 40 providing a source of heat within toleranced limits. One way of applying heat to the catheter body 36 is by passing the catheter body 36 through an oven, or through a fluid heat transfer medium for a time sufficient to permit the catheter body 36, or at least the radially outwardly extending portion of the catheter body 36, to soften to an extent which permits it to receive the reinforcing material 38 therewithin. Another way is by heating the reinforcing material which in turn heats the polymer.

As explained in the '324 patent, such a process had significant advantages in controlling the placement of the reinforcement material 38 in the wall of the catheter body 36 and thus is particularly suited for applications in which it is necessary to structure a catheter such that the reinforcing material 38 is located near the outer wall of the catheter, near the inner wall of the catheter, or at a precisely-controlled selected point in between. When it is remembered that catheter bodies are extremely small structures and catheter walls are extremely thin, such a process has significant advantages in assuring that the reinforced materials are embedded within the catheter wall throughout the length of the catheter while at the same time omitting the second extrusion step as previously discussed in connection with FIG. 1.

FIG. 5 and FIG. 6A–6F further illustrate the features of this aspect of the invention. Following the submersion of the reinforcing material 38 into the catheter body 36 mad from a thermoplastic polymer, the polymer thus softened and penetrated, but remaining outside the new smaller diameter of the reinforcement structure, produces a peaked or waffled contour, designated generally by the reference numeral 46 (FIG. 6C) in those locations where the polymer has exuded between the penetrating strands of the reinforcing material 38. The volume of polymer material from the reinforcement structure which is displaced is about equal to the volume of the reinforcing material 38 submerged in the catheter body. Thus, in FIG. 6C, the outside diameter of the composite catheter prior to application of the reinforcing material is designated by a dotted line by the reference numeral 47 to illustrate that in general the peaked areas 46 extend beyond the former outside diameter of the catheter body, while the valley areas formed near the wire (designated generally by the reference numeral 48) generally inwardly peak at the location of the reinforcing material 38 at a radially outwardly extending distance less than that of the former outside diameter 47 of the catheter body. Such a formed structure is advantageous in that in subsequent normal processing, the protruding portions 46 may be smoothed over in a sizing and/or smoothing step 44 to form a smooth catheter wall completely enveloping and embedding the reinforcement material 38 as seen in FIGS. 6E and 6F. More significantly, such a step avoids the application of a second extrusion.

According to one aspect of this invention, however, a catheter having an outside contour as shown in FIGS. 6C and 6D may be passed through an oversized die, or left merely so solidify or cure with the contour there shown. This leaves the irregular surface 46, 47 of the catheter 38 as the outer finished catheter surface. If the catheter does not pass through a die, (eliminating step 44) the effective contact area of the irregularity, i.e., "diamond" or "waffle" is determined by one or more lines at the largest effective O.D. Such line contact then determines the frictional engagement while fluid coupled to the guiding catheter.

Figure 9B:
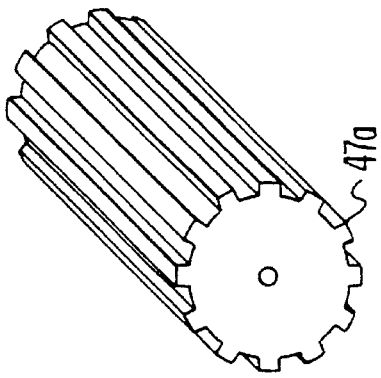
FIG. 9B shows the exterior surface of the tube made according to the prior art process of FIGS. 1 and 2 without the second pass.

On the other hand, if the surface of FIGS. 6C and 6D passes through an oversized die, a somewhat flattened outer surface is formed, as seen in FIG. 9B, where each protrusion has an upper area Ai so that the entire surface area at effective O.D. of the tubular catheter is $$A_n = \sum_{i=1}^{n} a_i$$

for a given length, and $A_n > A_o$, where $A_o = \pi d_o l$ of the original catheter of FIGS. 6E and 6F, where $d_o$ is the outer diameter and l is the length.

In another preferred aspect of the process according to the invention, the composite reinforced catheter body construction produced according to the invention may have the reinforcement material 38 intermittently applied, as in the prior art, or by continuously applying the reinforcement material and then excising portions thereof, or by periodically stopping the application of the reinforcement material, or continuously applying the reinforcement but in such a way as to cause the reinforcement material to lie along the outer surface of the composite structure as a series of straight line strands, as shown in FIGS. 8–10 of the '324 patent (herein incorporated by reference) as is there explained in greater detail. Such a straight line pattern is not submerged into the catheter wall body and thus is easily removed from the surface of the composite structure.

The process of the invention may be performed continuously utilizing conventional machinery. Thermoplastic polymer mandrels, extruders, and machines for applying reinforcing material, such as modified braiders, are known to the art. For example, braiding machines are available from either New England Butt Company or Wardwell Company, by way of example.

As specific examples of the type of thermoplastic plastic materials which may be used, such materials include polyethylene, polyurethane, certain rubbers, latexes and vinyls, conventionally available from such companies as DuPont. As a specific example of a preferred reinforcement material, one may use polyaramid, which is commercially available under the trademark "KEVLAR" but other materials such as carbon, boron fiber, glass, ceramic, non-metallic wires, metallic wires, and natural fibers such as cotton, as well as monofilaments such as nylon and polyester, may also be used. Where it is desired to utilize the reinforcement material as a conductor for signals, an electrically conductive wire may be used as all or any part of the reinforcement material.

The embodiment of FIG. 4 has been described with respect to the thermoplastic polymers forming the catheter body, using heat as the medium for controlling the plasticity of the wall to permit penetration of or deformation by the reinforcing material to form the waffled contour 46. In the alternative, as shown by the step bearing the reference numeral 49, other curable polymers may also be used. Where, for example, the polymer may be hardened by curing the cross-linking under the application of ultra-violet light, or by ionizing radiation, a curing step particular to the curable resin may be used. Such curable polymers may possess a sufficiently semi-rigid body characteristic prior to curing to permit penetration into, or deformation of, the surface by the application of the reinforcement material, as previously described, or to form the waffled contour without the application of heat at the reinforcing application as described in connection with FIG. 4. In those instances, the step of applying simultaneous heat may be eliminated in favor of a curing step, which may be a heating step, after the application of the reinforcement material and/or its partial excising as described and during or after sizing as shown in step 44. These alternative times of application of the curing step subsequent to the application of the reinforcement material to the catheter body being formed are designated generally by the two arrows connecting the block 49 to the process of FIG. 4. However, depending on the characteristics of the material used, a curing or partial curing step may be carried out either earlier or later in the process while carrying out the essential features of the invention.

Figure 7B:
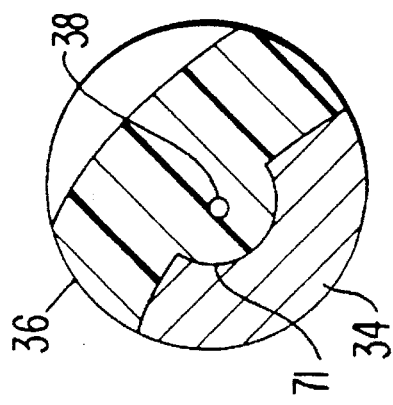
FIG. 7B shows an enlarged view of the same.
Figure 7A:
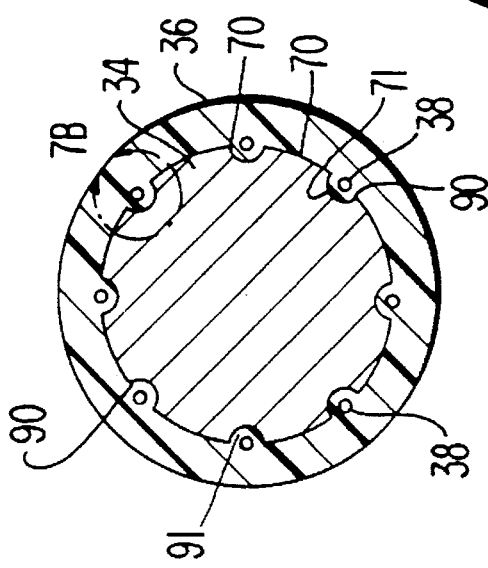
FIG. 7A shows in diagrammatic fashion a cross-sectional view of a mandrelized tube showing distortions of the interior wall of the tube and the exterior wall of the mandrel according to the process.

In still another preferred aspect of the invention, for the mandrelized embodiment of either FIGS. 2 to 5 made according to the processes of FIGS. 1 and 4 respectively, the reinforcing material can be caused to be positioned in the mandrelized tube as shown in FIG. 7, and in particular in FIG. 7A. Such an embodiment was discovered during experimental runs of steps in the '324 patent wherein it was learned that it is possible to insert the reinforcement "too deeply" within the wall, 36, to a location that is almost through the wall 36 into the lumen location, stopping just short of breaking through the interior wall 70. Since the mandrel 34 used during the processing is itself polymeric in nature, the heat softening of the structure wall 36, 70 as described above also carries slightly into the mandrel 34 as shown in the arc of the circle 90 defined by a locus of points equidistant from the outer surface of the reinforcing member 38. The result thus is that although the reinforcement strand 38 can be kept from passing completely through the structural wall 70 into the mandrel 34, the displacement of catheter body material ahead of the strand, i.e., in the partial annulus 91, can be made to carry into the outer surface or the mandrel 34 with the result that when the mandrel 34 is removed, the displacement of the tube wall into the mandrel shows as a radially raised ridge 71 of maximum height 72 directly, radially from the reinforcement strand.

Figure 7C:
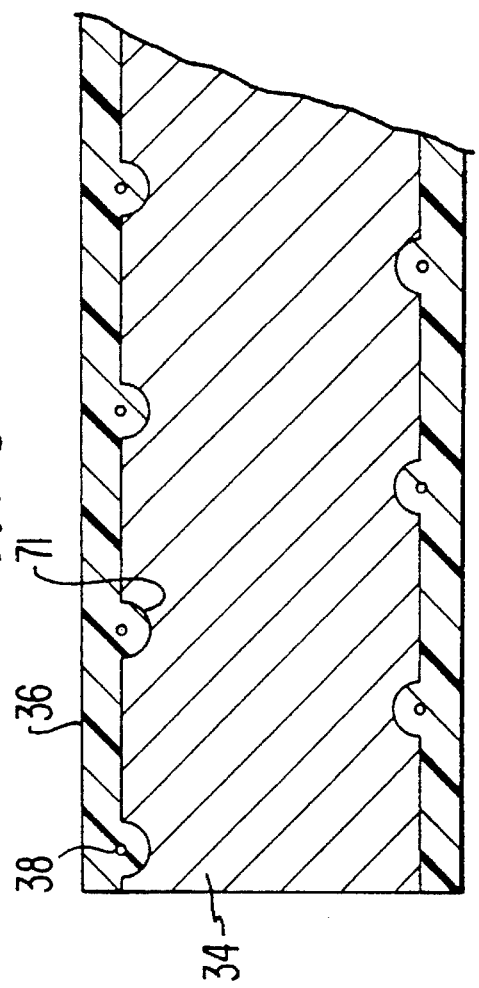
FIG. 7C shows an axial view of the same.

Moreover, as seen in FIGS. 7A to 7C, since the reinforcement strands 38 are almost always in the form of a helical wrap along the axis of the tube, the raised ridges 71 take the form of helices down the tubing with the "hand" of the innermost strand of set of strands as applied.

While not completely understood, the raised ridges assume a contour which is defined by about a locus of points of material equidistant from and having about the same shape as the reinforced strand. Thus, as seen in FIGS. 7A to 7C, the raised ridges 71 are defined by at least an arc of a circle and at most by a semicircle.

Figure 8B:
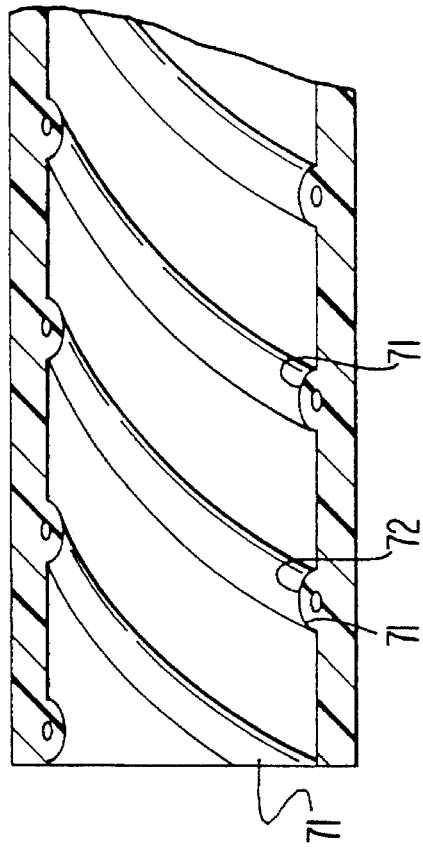
FIG. 8B shows an elongated axial section thereof showing the interior surface of the tube.
Figure 8A:
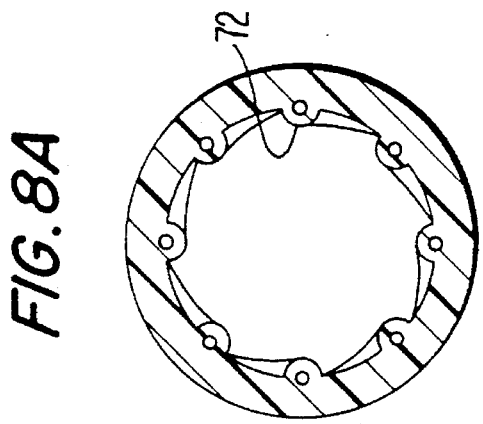
FIG. 8 shows in FIG. 8A a cross-sectional view of the tube after removal of the mandrel.

The interior wall of the catheter bore has a plurality such ridges 71, as seen in FIGS. 8A and 8B after the mandrel 34 is removed. The area of the high points is essentially a line contact 72, but if desired, though definitely not preferred, the ridges 72 could be smoothed and thus flattened somewhat to define an area having a relationship like that discussed for the outer relationship.

The method of FIG. 1 may also be used according to the teachings of the '324 patent so long as the exterior wall or interior wall exhibit the properties noted in this invention.

FIG. 8 illustrates in greater detail the features of the invention relating to the tube after removing the interior mandrel. Thus, the interior wall exhibits a "rifling" characteristic. As used, "rifling" is descriptive of the single-handed helical protrusion of the inner wall of a tubular structure due to the influence of the innermost of the two helices applied according to the '324 process in such a way as to almost breach the inner wall without doing so.

Figure 9A:
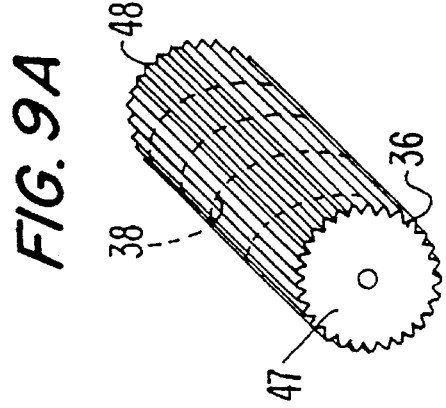
FIG. 9A shows the external surface made according to the processes of FIGS. 4 and 5 in a view similar to FIGS. 6C and 6D but unsized or sized by an oversized die.

FIGS. 9A and 9B show the exterior surface of the tube whether made according to the process of FIGS. 4–6 or according to the process of FIGS. 1 and 2. For example, for a tube made according to the process of FIGS. 4–6, thus producing a tube with a cross section and axial section shown in FIGS. 6C and 6D, the tube is sized with a sizing and smoothing die which is oversized. Thus, rather than produce a surface such as shown in FIGS. 6# and 6F, the surface is intentionally incompletely smoothed, leaving a pattern of smoothed-tip "waffles" or "diamonds" on the outside surface of the tube as shown in FIG. 9A. Such a rough surface tube would normally be discarded as unsuitable for vascular contact, but is advantageous in permitting the tube to slide concentrically down the lumen of an outer tube. Thus, the outer sheath of a tube so constructed exhibits the same low friction phenomena in the presence of fluid on the outside of the catheter as on the inside surface of the tube according to the invention. Accordingly, break up of fluid coupling occurs because of the waffled outer surface in a manner similar to the fluid coupling break up caused by the rifled interior surface as previously described. "Waffling" may be considered to be descriptive of the almost rectangular continuous pattern generated on the outer surface of a softened polymer structure by the passage through it of tensioned reinforcing strands. These strands are usually applied in the form of two, oppositely-handed helices of one or more strands each. As the strands are simultaneously wrapped into the tubed structure, each strand plows up a lineal distortion of the surface leaving a slightly depressed groove behind it as it sinks in. As these opposite-handed grooves cross each other, they leave a cross hatched pattern herein described as a "waffle" as well as raised "pillows" of polymer resulting from partial volumetric placement by the strand cross sections.

Finally, the method and apparatus according to the invention may exhibit both characteristics. That is, a tube made according to the invention may have the rifled inner tube as shown in FIGS. 8A and 8B, and the waffled outer surface as shown in FIGS. 9A so that the tube may be made for use as either a guiding catheter for a smaller interior catheter, or as a guided catheter in a larger tube.

Thus, an improved reinforced tube or catheter, and a method of making such an improved tube or catheter with superior interior and/or exterior surface characteristics has been described.

As a representative example, a catheter according to the invention has been made according to the teachings of the '324 patent and this application with an OD. of 0.104" and ID of 0.080" and a wall thickness of 0.012" having a wire reinforcement of 1 to 3 mils precisely embedded in the wall to produce the ID irregularity as described.

This invention will also provide a tubular catheter with a modified lumen and/or outside surface by modification of the prior art process of multiple layer extrusion. The lumen surface modification is accomplished at the time the reinforcing is being applied to the undersized "core" extrusion by use of a heated die located on the braiding machine slightly above the formation point of the braid.

This die is slightly smaller than the combined diameters of the first extrusion and the braid laying on its surface. The combination of the intentional interference fit and the heat of the die causes the reinforcement to be forced into the polymer structure as a path of least resistance. The heat present is controlled in degree so that the polymer layer is not fused completely. The compression of the reinforcement due to the heated die causes the braid to sink in to a predetermined level, but since the polymer is un-melted, that portion under the reinforcement strands is forced radially inward more that the polymer not directly under the reinforcement strand, thus reflecting the pattern of the braid without the reinforcement actually penetrating through the polymer layer and into the lumen. Upon removal of the temporary support mandrel from the lumen, the image of the braid pattern shows as a "waffle" of the lumen surface, the irregularity of which exhibits the friction reducing properties claimed in this invention.

Patterning the outside surface is accomplished during extrusion of the outer jacket by intentionally extruding at a lineal rate too fast to allow the melt to reach volumetric pressure equilibrium around the radially projecting portion of the reinforcement. This results in an outwardly projecting image of the reinforcement pattern, thus accomplishing the desired result of friction modification by contact area reduction.

A stainless steel reinforced polymer tube may also be provided which exhibits variable bending stiffness, with the variations occurring over the length of the tube at controlled locations and to a controlled degree and for a controlled axial length. The embodiment produced the following:

Embodiment specs:
Polymer Tube—0.081" ID×0.106 OD Pebax 72D
Reinforcing—001"×0.005" 304LV Stainless Flat Wire
Variable Pattern Density—10 to 32 picks or crosses/lineal inch axial The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are therefore intended to be embraced therein.

What is claimed is

1. A finished reinforced catheter made from a polymeric material and having a bore with an inner diameter and an outer diameter with a first reinforcement member wound in a first rotational direction to form a first helix and a second reinforcement member wound in a second helix in a second rotational direction which is opposite to said first rotational direction to form a second helix, said first and second reinforcement members being completely embedded within the wall of said catheter between said inner diameter and said outer diameter, said first reinforcement member being embedded sufficiently close to said inner diameter as to provide at least a ridge interrupting the smoothness of said inner diameter and following the contour of the reinforcement material located adjacent thereto, said ridge defining a land having an effective I.D. less than an actual I.D. of said interior diameter, so that when used as a guiding catheter, the effective friction force on an axially inserted or rotated concentric catheter is less than that exhibited by a smooth I.D. wall.

2. The catheter as set forth in claim 1, wherein said ridge has an arc-shaped cross section.

3. The catheter as set forth in claim 1, wherein said reinforcement member has a circular cross-section and said ridge is approximately semicircular.

4. The catheter as set forth in claim 1, wherein said reinforcement member comprises a flattened wire and wherein said flattened wire causes said ridge to have a raised band shape due to use of a flattened wire with one axis of a length greater than the other.

5. The catheter as set forth in claim 1, further comprising a plurality of such ridges spaced about along the interior of the inner diameter bore of said catheter.

6. A method of using the catheter of claim 1 as a guiding catheter comprising the steps of providing the catheter as defined in claim 1, and passing another catheter therethrough whereupon contact between the outer surface of said passing catheter and said guiding catheter is defined by said interior ridge, thus reducing fluid coupling therebetween.

7. The catheter as set forth in claim 1, wherein said outer diameter further includes an irregular surface, said irregular surface reducing the friction between said outer diameter and another tubular member when said catheter is guided through said another tubular member.

8. The catheter as set forth in claim 1, wherein said outer diameter further includes an irregular surface, said irregular surface reducing the friction between said outer diameter and a ridged internal wall of a lumen when said catheter is guided through the lumen having the ridged internal lumen wall.

* * * * *